Figure 1:
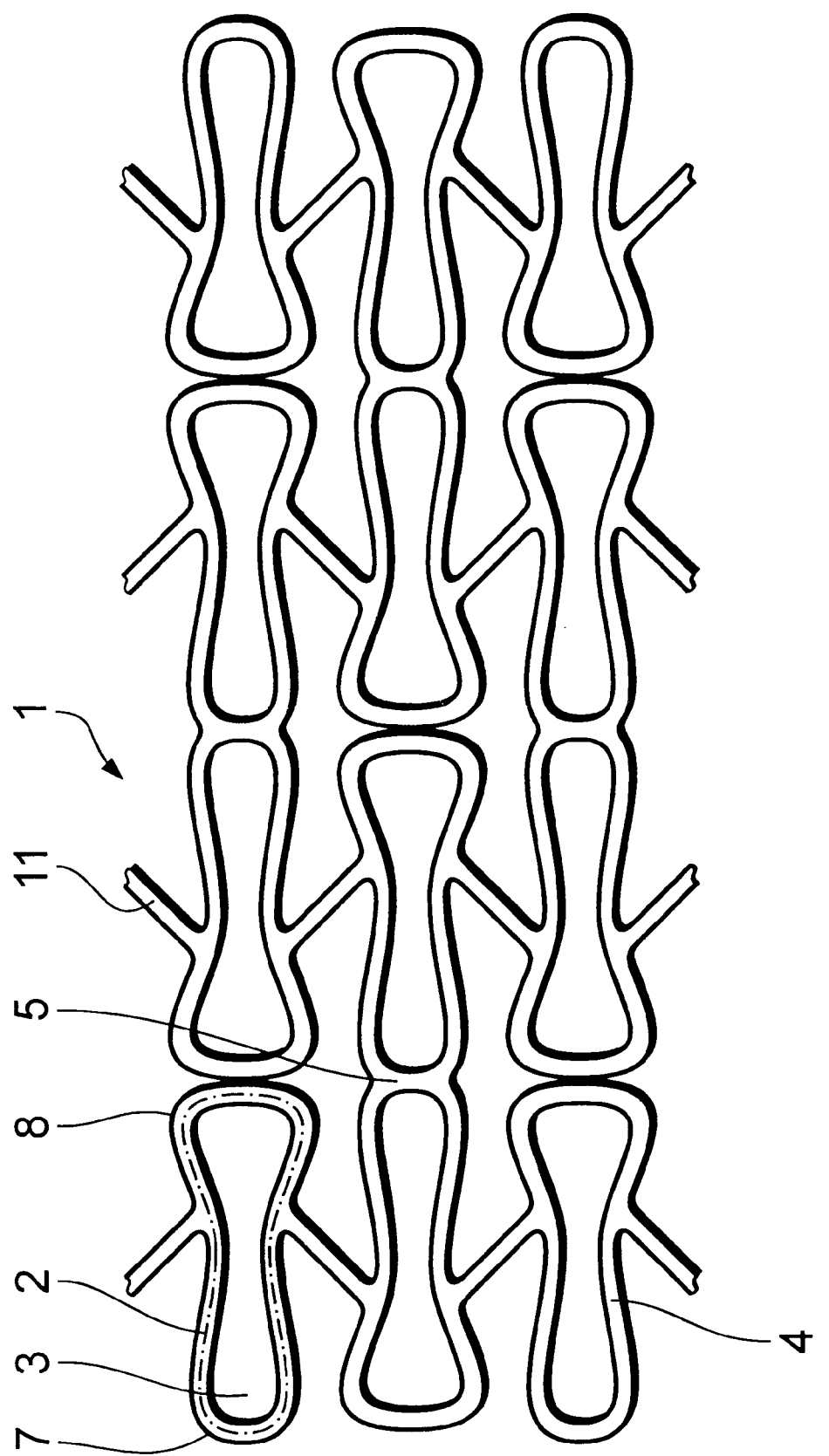

United States Patent [19]
Kranz

[11] Patent Number: 5,968,093
[45] Date of Patent: Oct. 19, 1999

[54] STENT

[75] Inventor: Curt Kranz, Berlin, Germany

[73] Assignee: Biotronik Mess-and Therapiegerate GmbH & Co., Berlin, Germany

[21] Appl. No.: 09/101,036
[22] PCT Filed: Oct. 28, 1997
[86] PCT No.: PCT/DE97/02576
    § 371 Date: Jun. 29, 1998
    § 102(e) Date: Jun. 29, 1998
[87] PCT Pub. No.: WO98/18406
    PCT Pub. Date: May 7, 1998

[30] Foreign Application Priority Data

Oct. 28, 1996 [DE] Germany .............................. 196 45 288
Dec. 10, 1996 [DE] Germany .............................. 196 53 718

[51] Int. Cl.[6] ........................................................ A61F 2/06
[52] U.S. Cl. .................................. 623/1; 623/12; 606/198
[58] Field of Search ............................ 623/1, 12; 609/198

[56] References Cited

U.S. PATENT DOCUMENTS

| 5,449,373 | 9/1995 | Pinchasik et al. ........................... 623/1 |
| 5,591,197 | 1/1997 | Orth ............................................. 623/1 |
| 5,810,872 | 9/1998 | Kanesaka et al. ........................... 623/1 |
| 5,879,381 | 3/1999 | Moriuchi et al. ........................... 623/1 |

*Primary Examiner*—David H. Willse
*Assistant Examiner*—Suzette Jackson
*Attorney, Agent, or Firm*—Venable; George H. Spencer; Ashley J. Wells

[57] ABSTRACT

A stent, especially a coronary stent, comprising at least one thin-walled, tubular member with an openly reticular outer surface containing recesses, which are defined by narrow weblike members. Weblike members are formed from the remaining material from the tube wall once the material has been removed from the recess area. The weblike members are shaped in such a way as to substantially reduce the deformation to which a weblike member is subjected between connecting areas with other weblike members during expansion. The invention also relates to a method of producing the like.

18 Claims, 3 Drawing Sheets

STENT

The invention relates to a stent, particularly a coronary stent, as an intraluminal expansion element of the type mentioned in the generic part of claim 1, and to methods of making such a stent.

An expandable intraluminal element with at least one thin-walled, tubular member (hereinafter referred to as a stent) is known from European patents EP-B1 0 364 787 and EP-B1 335 341. The generated surface of the stent is in the form of an open network and has apertures bounded by strap-like elements of low material thickness, extending in a straight line in the axial and peripheral directions. The strap-like elements comprise the remaining wall of the tube, from which the material in the area of the apertures has been removed.

During an operation such stents are expanded by the action of outwardly directed forces, by means of a tubular dilator working with compressed gas. The stent retains its tubular shape in spite of deformation and expands the vessel which has been narrrowed by deposits.

The known stent has the drawback that expansion through deformation of the axially extending strap-like elements can only take place to a limited extent, as relatively narrow limits are set to a change in the shape of the individual strap-like elements of the stent. These limits depend on the material tensions which accompany deformation, and which may lead to breakage of one or more of the strap-like elements forming the network if the deformation becomes too great.

For safety reasons therefore deformation must normally be kept far below a possible danger range, as breakage of a strap would cause its free ends in the vicinity of the breakage point to project into the interior of the vessel provided with the stent. The concomitant danger of restenosis formation would not only put the success of the operation into question but also endanger the patient's life.

Based on the defects of prior art, the problem of the invention is to provide an expandable stent of the above type, which can be expanded as safely as possible—and thus without any risk of breakage in the vicinity of the strap-like element through tensile overloading. Shortening of the stent must also be avoided.

The problem is solved by the characterising features of claim 1.

The invention includes the technical teaching that, in the case of fragile tubular elements which are made of suitable materials, which have network-like structures and which are subject to deformation in use, critical loads on the material or even breakages of the material can be avoided, if the maximum tensions occurring in areas subject to increased deformation are limited from the outset by the design. Shortening of the stent during its expansion may also be avoided if, in addition, pairs of transversely expandable elements are directly joined at the ends longitudinally of the stent, each of the two expandable elements, in the form of a flattened ring element made up of straps, being joined transversely by a strap-like element to another transversely expandable element, which is itself not directly joined at the end to another expandable element, which is in turn joined by a strap-like element to one of the first-mentioned, transversely expandable elements, the strap-like elements each being inclined to the transverse direction at an angle such that this angle is reduced on expansion of the stent, and the non-joined adjacent ends of transversely expandable elements thus move away from each other.

This applies particularly if the strap-like elements in the non-expanded stent are at an inclination of substantially 45° to the transverse direction.

Through the process of stretching the expandable elements transversely of the stent, which occurs simultaneously with the expansion of the stent, and through the alignment of the inclined joining elements in the transverse direction, the non-joined groups of expandable elements are displaced relative to each other, in such a way that that movement compensates for the shortening of the stent by extending the flat shapes of the expandable elements into O rings.

The transversely expandable elements interact particularly favourably with the strap-like elements if the latter lead into the transversely expandable elements at an angle of less than 45°—relative to their local direction.

If the strap-like elements are curved so as to lead into the strap regions of the expandable elements perpendicularly in the centre, a particularly favourable input of forces is obtained.

Owing to the geometry of the arrangement in the non-expanded condition, it is beneficial for the rounding of the transversely expandable elements, in the end region where they are joined at the end to the next similar element in the longitudinal direction, to have a larger radius than at the end where they are not joined.

If the transversely expandable elements have an ellipse-like or circle-like shape in the expanded condition of the stent, the input of force into the expanded vessel is particularly harmonious.

This also applies if the strap-like elements substantially act on regions of the transversely expandable element which are opposite each other in the transverse direction—and particularly if they act on them substantially centrally—when the stent is expanded.

A particularly beneficial construction can be obtained, not merely by designing for the greatest possible strength by enlarging the cross-sections of the material, but also by optimising the shape of the straps and joining regions with a view to the expected loads. This can be done, on the one hand by locally minimising the maximum tensions occurring, but on the other hand by also controlling the necessary deformations.

These relationships are described in a patent application filed at the same time by the same Applicant.

As an advantageous precondition for the design it has been found that deformation is assisted if the shape of the stent in the non-expanded condition substantially corresponds to the shape obtained when a sample, which has strap structures of regular shape in its expanded shape and which is made in that form from a tubular structure, is compressed into the non-expanded shape, the eventual starting shape. Thus the form produced as the starting shape corresponds to that obtained by compressing a stent which was made in the expanded form.

Such regular shapes are preferably produced from circles, ellipses, rectangles, squares, polygons or structures combining these and/or approximating to them.

To encourage local tension-free deformations, branches from straps are formed so as to avoid abrupt changes in the strap width. The appearance of stress concentrations or notch tensions and the like is thus avoided. In this way material tensions, particularly in the region of intersections or branches, can be prevented from exceeding a predetermined value on deformation, even as a notch tension.

A construction of this type gives the branches of strap-like elements a particularly organic shape, substantially corresponding to the shape of branches from tree trunks.

In some cases it is beneficial for the strap-like elements forming links between expandable elements to be substantially S-shaped, as areas of maximum deformation are then transposed from the lead-in or joining areas to the free areas of strap.

It is further advantageous for areas of intersections also to be shaped so that a maximum change in the angle between adjacent strap-like elements forming arms of a cross or branches is not exceeded for a predetermined expansion. This can preferably be done by giving strap-like elements forming the arms of a cross or branches a curved shape.

If the edges of strap-like elements have rounded portions in an intersecting or branching area or in the area of a joining region linking successive stent segments, so that sharp corners are avoided, the maximum tensions here will be limited.

In a preferred embodiment of the invention the expandable, substantially hollow cylindrical stent, with a generated surface which is given a network structure by apertures, has an organic conformation at the points joining the strap-like elements which bound the apertures, in order to avoid a high notch tension there which might lead to breakage. Local breakage of the stent detrimentally produces free, relatively sharp-edged ends within the spatial configuration of the stent, which may on the one hand bore through the wall of the vessel, or on the other hand reduce the free cross-section of the vessel by moving out into the bloodstream.

This conformation is characterised by a rounding of all points linking the strap-like elements which move relative to each other on expansion of the stent; it ensures, in a simple and at the same time advantageous manner, that the amount of local deformation of the material at the points in the stent construction which are critical in respect of the tensile strain occurring when the stent is extended has a minimal value, through uniform distribution of the deformation work.

Coupling members in the form of cruciform, strap-like elements are provided to join the individual strap-like elements extending substantially axially and bounding the apertures; these members interconnect adjacent apertures in an axial direction, in each case at their ends and in a tangential direction, always at the centre of the axially extending strap-like elements.

In a preferred embodiment of the invention the arms of the cruciform coupling members are curved and arranged so that they form the sides of a substantially obtuse angle in the tangential direction and a substantially acute angle in the axial direction. The strap-like elements of the apertures, adjoining the arms of the coupling members, are shaped as an axially extended S, and the opposing strap-like elements adjacent each other in a tangential direction are arranged symmetrically in mirror image.

In another embodiment of the invention with this configuration of the coupling member, rounding of the material is advantageously provided at the point of intersection, so that there is only a relatively slight change in the angle subtended by the adjacent arms of the cruciform coupling member on expansion of the stent. Consequently there is not a high notch tension at the intersection and in particular there are no local tension peaks, so that any risk of breakage on expansion is excluded.

With the same end in view, the free sections of the apertures at the ends of the stent, or at the ends of the stent segments in the above-described embodiments of the invention, are curved so that only slight mechanical stresses arise in those areas too on expansion of the stent, and no extreme notch tension values occur.

The above-described construction of the surface of the stent according to the invention, with organic shapes, ensures substantially even distribution of the deformation work done in the expansion process to the respective aperture-bounding sections, and thereby avoids extreme tensile stresses on individual points or areas on the stent surface.

To enable stenoses in curved blood vessels to be successfully treated by expanding stents, the stent in another favourable embodiment of the invention is divided into substantially identically shaped segments arranged in rows in an axial direction.

A preferred stent designed in the above manner is made of tantalum as the material, and is provided with a coating of amorphous silicon carbide.

Other advantageous further embodiments of the invention are characterised in the sub-claims and will now be explained in greater detail with reference to the accompanying drawings, together with the description of the preferred embodiment.

Figure 2:
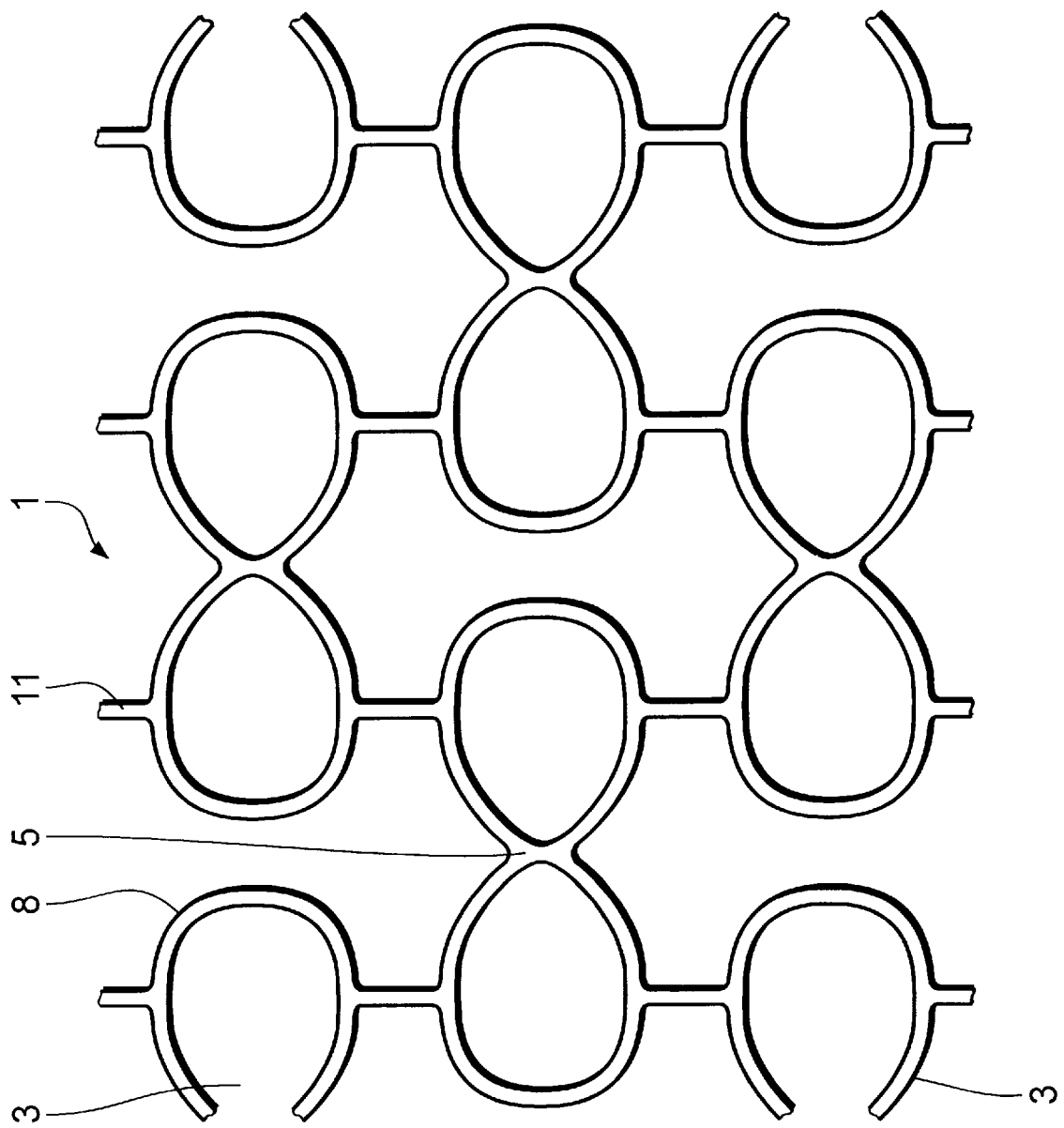
Figure 3:
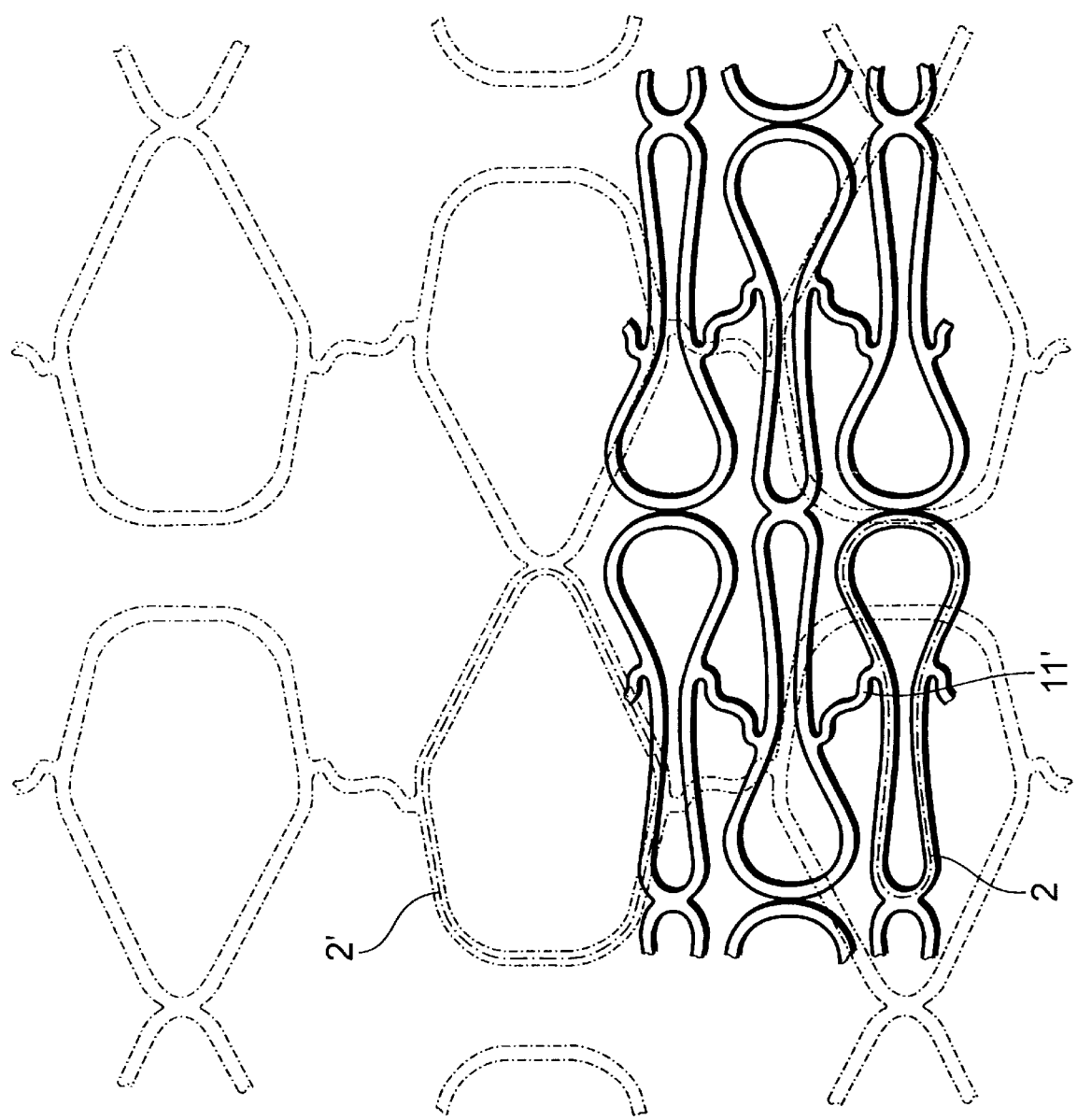

In the drawings:

FIG. 1 represents a development of the non-expanded stent structure as the preferred embodiment, shown as a development of the invention in side elevation, FIG. 2 shows the stent structure from FIG. 1 in the expanded condition, and FIG. 3 shows the conditions in FIGS. 1 and 2 superimposed for comparison.

A stent 1 reproduced in FIG. 1 basically has a tubular/hollow cylindrical shape with numerous openings surrounded by expandable structural elements in the form of flattened rings. These will hereinafter be termed "expandable elements", and an example of them is marked with a dash-and-dot line 2. The expandable elements 2 are formed by narrow strap-like regions 4 of square cross-section running round them, and are distinguished by the fact that they enclose an aperture 3 in an annular shape. The elements 2, in the fully expanded condition in this case, have almost the shape of a circle or an ellipse. It will be seen that the shape in the non-expanded condition is derived from that in the expanded condition, although the stent never assumed that condition in its production. The shape was discovered in a simulated process—based on an ideal shape to be adopted in the expanded condition—with compression simulated in a mathematical model. As the material sets up uniform resistance to mechanical forces acting on it when compression is applied, local deformations are also evened out. Uniform arcs with maximal radii are formed rather than localised sharp bends. The resultant shape forms the basis for modelling the non-expanded one, which can thus be converted to the required final shape in the reverse direction with uniform local deformation.

The strap-like regions 4 surrounding an expandable element are structured with a multiple S-like sweep. They each surround an aperture 3, in such a way that tangentially adjacent, opposing, strap-like regions 4 of the same or an adjacent aperture 3 are arranged symmetrically in mirror image. The ends of the expandable elements 2 in the longitudinal direction have free arcuate regions 7 and 8 which are more curved.

The expandable elements are shaped so that, when the stent has been inserted in a vessel, they can be converted to a ring shape with minimum deformation by dilation with a balloon catheter The arc 8 can be seen to assume a maximal radius. The opposing S-shaped arcs enable it to incur minimum deformation when expanded.

Joining regions 5 are provided between apertures 3 arranged adjacent each other in axial (longitudinal) and tangential (transverse) directions on the generated surface of the stent 1, and mechanically couple the respective expandable regions 2. Rounding of the material is provided in the crossing, joining region 5, so that the region has an organic shape, reducing the occurrence of increased notch tensions.

The individual strap-like elements can be seen to be shaped so that the bending deformation to which such an element is subjected on expansion within the hollow cylindrical, tubular shape—resulting from the integral of the local changes of angle on deformation, determined over the length of the respective element between adjoining regions linking it with other strap-like elements—is distributed over the length of the element so that a predetermined strain on the material is not exceeded even locally.

The shape of the stent in the non-expanded condition substantially corresponds to the shape obtained when a sample, which has regularly shaped strap structures in its expanded shape and which is made in that form from a tubular structure, is compressed into the non-expanded shape—the eventual starting shape. The regular shape comprises circles, ellipses, rectangles, squares, polygons or structures combining these and/or approximating to them.

Branches of straps are formed so as to avoid abrupt changes in the width of the strap and so that tensions on the material, particularly in the region of the branching, do not exceed a predetermined value on deformation even as a notch tension. The stent represented in FIG. 1a is of substantially homogeneous structure over its whole length.

In the embodiment illustrated it will be seen that pairs of transversely expandable elements are directly joined at the ends longitudinally of the stent, each of the so expandable elements, in the form of a flattened ring element made up of straps, being joined transversely by a strap-like element to another transversely expandable element; the latter element is itself not directly joined at the end to another expandable element, which is in turn joined by a strap-like element to one of the first-mentioned, transversely expandable elements; the strap-like elements are each inclined to the transverse direction at an angle which is reduced on expansion of the stent, and the non-joined adjacent ends of transversely expandable elements thus move away from each other, so that shortening of the stent during its expansion can be avoided.

In the non-expanded stent the strap-like elements are inclined to the transverse direction at substantially 45°.

Through the process whereby the expandable elements are stretched transversely of the stent simultaneously with the expansion of the stent, and through the alignment of the inclined joining elements in the transverse direction, the non-joined groups of expandable elements are displaced relative to each other so that their movement compensates for the shortening of the stent with the stretching of the flat shapes of the expandable elements into O rings.

FIG. 2 uses the same references as FIG. 1; it will be seen from it how the FIG. 1 structure is transformed in the expanded condition to a structure with substantially round rings linked by straps. The joining straps between the expandable elements are now aligned substantially tangentially.

In addition, the individual strap-like elements can be seen to be shaped so that the bending deformation to which an element is subjected on expansion within the hollow cylindrical, tubular shape—resulting from the integral of the local changes of angle on deformation, determined over the length of the respective strap-like element between adjoining regions linking it with other strap-like elements—is distributed over the length of the element so that it does not exceed a predetermined value locally.

It will also be seen that branches of straps are formed so as to avoid abrupt changes in the width of the strap and so that tensions on the material, particularly in the region of the branch, do not exceed a predetermined value on deformation, even as notch tensions.

The constriction of the stent 1 described above allows the tubular stent to expand without the notch tension reaching extreme values at the joints, leading to the breaking of strap regions.

As will be seen from FIG. 2 the maximum local deformations—and thus the danger of extreme notch tension values being reached on expansion of the segment 2—remain extremely low. Instead of being concentrated on individual points of individual apertures 3, particularly the tip of the external arcuate pieces 7, they extend over the whole region of the apertures 3 bounded by the S-shaped strap-like elements 4 and the arms 5.1, 5.2, 5.3. 5.4 of the joining regions 5.

Above all it will be seen that an expandable element formed by strap elements is deformed with local deformations being limited as far as possible. The arcuate regions in the non-expanded condition are chosen as large as possible, so that when the stent is expanded all parts of the strap-like element are as far as possible equally involved in the re-shaping.

In FIG. 3 the structure of the non-expanded stent from FIG. 1 and the expanded stent from FIG. 2 are superimposed; it will be seen not just that no shortening of the stent occurs but that there is even a certain lengthening, although on further expansion this is compensated for by the return of the stent to its original length. Its application virtually free of complications is thus ensured. In the embodiment shown in this figure the strap-like joining element 11' is curved doubly in an S shape in order to minimise deformations.

The stent illustrated here is made of tantalum, titanium or another biocompatible alloy, as a material giving good compatibility with the body and excellent deformability. A micro-coating of amorphous silicon carbide counteracts thrombus formation.

The forms taken by invention are not restricted to the preferred embodiments described above. There are in fact a number of favourable versions which make use of the illustrated solution in fundamentally different ways.

I claim:

1. A stent, particularly a coronary stent, comprising at least one thin-walled, tubular element, the generated surface of which is in the form of an open network and has apertures bounded by narrow, strap-like elements, the strap-like elements being formed from the remaining material of the tubular wall from which the material in the area of the apertures was removed, characterised in that pairs of transversely expandable elements are directly joined at the ends longitudinally of the stent, each of the two expandable elements, in the form of a flattened ring element made up of straps, being joined transversely by a strap-like element to another transversely expandable element, which is itself not directly joined at the end to another expandable element, which is in turn joined by a strap-like element to one of the first-mentioned, transversely expandable elements, the strap-like elements each being inclined to the transverse direction at an angle such that this angle is reduced on expansion of the stent, and the non-joined adjacent ends of transversely expandable elements thus move away from each other.

2. A stent according to claim 1, characterised in that when the stent is not expanded the strap-like elements have an inclination of substantially 45° to the transverse direction.

3. A stent according to claim 1, characterised in that the strap-like elements lead into the transversely expandable elements at an angle of less than 45'.

4. A stent according to claim 1, characterised in that the strap-like elements are curved so as to lead in perpendicularly in the centre.

5. A stent according to claim 1, characterised in that the rounding of the transversely expandable elements in the end region where they are joined at the end to the next similar element in the longitudinal direction has a larger radius than at the end where they are not joined.

6. A stent according to claim 1, characterised in that in the expanded condition of the stent the transversely expandable elements have an ellipse-like or circle-like shape.

7. A stent according to claim 1, characterised in that when the stent is expanded the strap-like elements substantially act on regions of the transversely expandable element which are opposite each other in the transverse direction.

8. A stent according to claim 7, characterised in that the strap-like elements exert their action substantially centrally.

9. A stent according to claim 1, characterised in that the strap-like elements are shaped so that the total deformation which a strap-like element undergoes between joining regions to other strap-like elements in the expansion process is substantially minimised.

10. A stent according to claim 1, characterised in that the individual strap-like elements are shaped so that the bending deformation to which a strap-like element is subjected on expansion within the hollow cylindrical, tubular shape, resulting from the integral of the local changes of angle on deformation, determined over the length of the respective strap-like element between adjoining regions with other strap-like elements, is distributed over the length of the element so that it does not exceed a predetermined value locally.

11. A stent according to claim 1, characterised in that the bending deformation applied to a length of one-fifth of a strap-like element is no greater than a quarter of the total bending deformation to which that element is subjected.

12. A stent according to claim 1, characterised in that the shape of the stent in the non-expanded condition substantially corresponds to the shape obtained when a sample, which has strap structures of regular shape in its expanded shape and which is made in that form from a tubular structure, is compressed into the non-expanded shape, the eventual starting shape.

13. A stent according to claim 12, characterised in that the regular shape comprises circles, ellipses, rectangles, squares, polygons or structures combining these and/or approximating to them.

14. A stent according to claim 1, characterised in that branches from straps are formed avoiding abrupt changes in the strap width.

15. A stent according to claim 1, characterised in that branches are formed so that the material tensions, particularly in the region of the branching, do not exceed a predetermined value on deformation, even as a notch tension.

16. A stent according to claim 1, characterised in that the strap-like elements (4, 11') are substantially S-shaped.

17. A stent according to claim 1, characterised by titanium, tantalum or another biocompatible metal or a corresponding metal alloy as the material.

18. A stent according to claim 17, characterised in that a coating of amorphous silicon carbide is provided.

* * * * *